(12) United States Patent
Hossainy et al.

(10) Patent No.: US 7,311,980 B1
(45) Date of Patent: *Dec. 25, 2007

(54) POLYACTIVE/POLYLACTIC ACID COATINGS FOR AN IMPLANTABLE DEVICE

(75) Inventors: Syed F. A. Hossainy, Fremont, CA (US); Yiwen Tang, San Jose, CA (US); Gina Zhang, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 10/910,453

(22) Filed: Aug. 2, 2004

(51) Int. Cl.
B32B 27/06 (2006.01)
B32B 27/08 (2006.01)
B32B 27/36 (2006.01)
A61F 2/02 (2006.01)
A61F 2/04 (2006.01)

(52) U.S. Cl. ............... 428/480; 428/357; 428/36.9; 428/36.91; 623/1.42; 623/1.43; 623/1.44; 623/1.46; 623/1.49

(58) Field of Classification Search .............. None
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,778,467 A * | 10/1988 | Stensaas et al. | 623/23.64 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,100,992 A | 3/1992 | Cohn et al. | 424/501 |

(Continued)

FOREIGN PATENT DOCUMENTS

DE 42 24 401 1/1994

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Vivian Chen
(74) *Attorney, Agent, or Firm*—Squire Sanders & Dempsey LLP (57) ABSTRACT

A polymeric coating for a medical device that comprises poly(lactic acid) and a block copolymer including blocks of poly(ethylene glycol) and poly(butylene terephthalate) is provided.

12 Claims, 3 Drawing Sheets

U.S. PATENT DOCUMENTS

| | | | |
|---|---|---|---|
| 5,112,457 A | 5/1992 | Marchant | 204/165 |
| 5,133,742 A | 7/1992 | Pinchuk | 623/1 |
| 5,163,952 A | 11/1992 | Froix | 623/1 |
| 5,165,919 A | 11/1992 | Sasaki et al. | 424/488 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | 378/64 |
| 5,508,036 A * | 4/1996 | Bakker et al. | 424/424 |
| 5,516,881 A | 5/1996 | Lee et al. | 528/320 |
| 5,569,463 A | 10/1996 | Helmus et al. | 424/426 |
| 5,578,073 A | 11/1996 | Haimovich et al. | 623/1 |
| 5,580,923 A * | 12/1996 | Yeung et al. | 525/54.1 |
| 5,581,387 A | 12/1996 | Cahill | 359/137 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,644,020 A | 7/1997 | Timmermann et al. | 528/288 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,861,387 A | 1/1999 | Labrie et al. | 514/169 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,948 A * | 11/1999 | Goedemoed et al. | 424/489 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |

| Patent Number | Date | Inventor | Class |
|---|---|---|---|
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 514/252.1 |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Castro et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B2 | 7/2004 | Chen et al. | 424/423 |
| 6,896,965 B1* | 5/2005 | Hossainy | 428/411.1 |
| 7,005,137 B1* | 2/2006 | Hossainy et al. | 424/423 |
| 2001/0007083 A1 | 7/2001 | Roorda | 623/1.15 |
| 2001/0014717 A1* | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falitico | 623/1.21 |
| 2002/0007215 A1 | 1/2002 | Falotico et al. | 623/1.21 |
| 2002/0009604 A1* | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1* | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1* | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |
| 2005/0106204 A1* | 5/2005 | Hossainy et al. | 424/423 |
| 2005/0112170 A1* | 5/2005 | Hossainy et al. | 424/423 |
| 2005/0143808 A1* | 6/2005 | Hossainy et al. | 623/1.42 |
| 2005/0191332 A1* | 9/2005 | Hossainy | 424/423 |
| 2005/0232971 A1* | 10/2005 | Hossainy et al. | 424/426 |
| 2005/0233062 A1* | 10/2005 | Hossainy et al. | 427/2.1 |
| 2005/0245637 A1* | 11/2005 | Hossainy et al. | 523/113 |

| | | | | | | |
|---|---|---|---|---|---|---|
| 2006/0093842 | A1* | 5/2006 | DesNoyer et al. | 428/474.4 | WO | WO 04/009145 | 1/2004 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995)

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarboxylic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteritics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997)

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

POLYACTIVE/POLYLACTIC ACID COATINGS FOR AN IMPLANTABLE DEVICE

BACKGROUND OF THE INVENTION

1. Field of the Invention

This invention generally relates to a polymeric coating for an implantable device such as a drug eluting or delivery stent.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient. One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer. One such polymeric carrier is a coating composition based on polylactic acid (PLA).

Figure 1A:
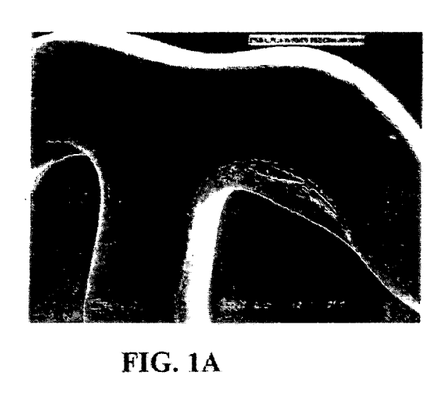
FIGS. 1A and 1B illustrate a stent coated with pure poly(D,L-lactic acid) (PDLLA) after wet expansion having some polymer peeling off at high strain regions.
Figure 1B:
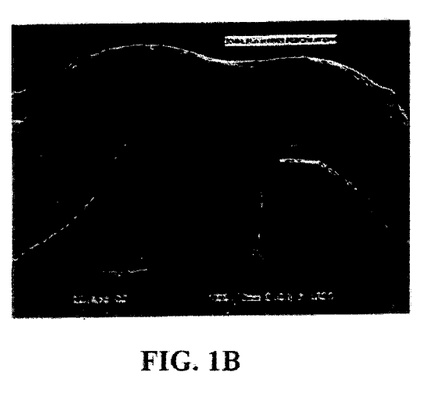

Many of the biocompatible polymeric carriers used in the art of drug delivery have relatively high glass transition temperatures ($T_g$) and relatively small range of elongation. For example, PLA of a molecular weight of 100,000 Daltons has a $T_g$ of about 51° C., and a range of elongation of about 4%, which renders a coating formed of PLA hard and inflexible. When a composition of such a polymer is used for coating an implantable device, certain undesirable side effects may develop in the course of using such an implantable device because, in the process of implantation, an implantable device is often physically manipulated, e.g., expanded or deformed, leading to damages to the coating. FIGS. 1A and 1B show a stent coated with PDLLA after wet expansion that having some polymer peeling off at the high strain joints.

Therefore, there is a need for a coating of an implantable device that provides a controlled release of a bioactive agent and improved mechanical properties.

The compositions and the coatings formed thereof disclosed herein address the above described problems and needs.

SUMMARY OF THE INVENTION

A polymeric coating for an implantable device that includes a biocompatible polymer, a biobeneficial material and optionally a bioactive agent is disclosed. In some embodiments, the biocompatible polymer, the biobeneficial material, and optionally the bioactive agent can be in the form of a blend. In some other embodiments, the coating can include a layer of the biocompatible polymer that may optionally include the bioactive agent, a layer of the biobeneficial material coated beneath and/or over the layer of the biocompatible polymer that may optionally include the bioactive agent. In still some other embodiments, the coating can include a layer of the bioactive agent, a layer of the biocompatible polymer coated beneath and/or over the bioactive agent layer, and a layer of the biobeneficial material coated beneath and/or over the layer of the bioactive agent layer and/or the biocompatible polymer. The layer of the biocompatible polymer can be capable of binding the bioactive agent to the surface of the implantable device.

As compared to a coating formed of the biocompatible polymer, the coating disclosed herein has comparable or improved mechanical properties and improved surface properties. The disclosed coating also has improved drug eluting or releasing properties The implantable device can be any implantable device such as a stent. The medical can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Coatings on Implantable Devices

A polymeric coating for an implantable device that includes a biocompatible polymer, a biobeneficial material and optionally a bioactive agent is disclosed. In some embodiments, the biocompatible polymer, the biobeneficial material, and optionally the bioactive agent can be in the form of a blend or mixture. In some other embodiments, the coating can include a layer of the biocompatible polymer that may optionally include the bioactive agent, a layer of the biobeneficial material coated beneath and/or over the layer of the biocompatible polymer that may optionally include the bioactive agent. In still some other embodiments, the coating can include a layer of the bioactive agent, a layer of the biocompatible polymer coated beneath and/or over the bioactive agent layer, and a layer of the biobeneficial material coated beneath and/or over the layer of the bioactive agent layer and/or the biocompatible polymer. Any combination of layering can be used. The layer of the biocompatible polymer can be capable of binding the bioactive agent to the surface of the implantable device.

As compared to a coating formed of the biocompatible polymer, the coating embodiments disclosed herein have comparable or improved mechanical properties and improved surface properties. The disclosed coating embodiments also have improved drug eluting or releasing properties. The disclosed coating is capable of controlled release of a bioactive agent.

Biobeneficial Material

The biobeneficial material useful in the coatings described herein can be a polymeric material or non-polymeric material. The biobeneficial material is preferably flexible and biocompatible and/or biodegradable (a term which includes biodegradable and bioabsorbable), more preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Generally, the biobeneficial material has a relatively low glass transition temperature ($T_g$), e.g., a $T_g$ below or significantly below that of the biocompatible polymer, described below. In some embodiments, the $T_g$ is below human body temperature. This attribute would, for example, render the biobeneficial material relatively soft as compared to the biocompatible polymer and allows a layer of coating containing the biobeneficial material to fill any surface damages that may arise when an implantable device coated with a layer comprising the biocompatible polymer. For example, during radial expansion of the stent, a more rigid biocompatible polymer can crack or have surface fractures. A softer biobeneficial material can fill in the crack and fractures.

Another attribute of a biobeneficial material is hydrophilicity. Hydrophilicity of the coating material would affect the drug release rate of a drug-delivery coating and, in the case that the coating material is biodegradable, would affect the degradation rate of the coating material. Generally, the higher hydrophilicity of the coating material, the higher the drug release rate of the drug-delivery coating and the higher the degradation rate of the coating if it is biodegradable.

Representative biobeneficial materials include, but are not limited to, polyethers such as poly(ethylene glycol), copoly(ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof. In some embodiments, the polymer can exclude any one of the aforementioned polymers.

In a preferred embodiment, the biobeneficial material is a block copolymer having flexible poly(ethylene glycol) and poly(butylene terephthalate) blocks (PEGT/PBT) (e.g., PolyActive™). PolyActive™ is intended to include AB, ABA, BAB copolymers having such segments of PEG and PBT (e.g., poly(ethylene glycol)-block-poly(butylene-terephthalate)-block poly(ethylene glycol) (PEG-PBT-PEG).

These segments are biocompatible, non-toxic, non-antigenic and non-immunogenic. Studies have shown that the PolyActive™ decreases thrombosis and embolism formation. PolyActive™ is generally expressed in the form of xPEGyPBTz, in which x is the molecular weight of PEG, y is percentage of PEGT, and z is the percentage of PBT. A specific PolyActive™ polymer can have various ratios of the PEG, ranging from about 1% to about 99%, e.g., about 10% to about 90%, about 20% to about 80%, about 30% to about 70%, about 40% to about 60% PEG. The PEG for forming PolyActive™ can have a molecular weight ranging from about 300 Daltons to about 100,000 Daltons, e.g., about 300 Daltons, about 500 Daltons, about 1,000 Daltons, about 5,000 Daltons, about 10,000 Daltons, about 20,000 Daltons, or about 50,000 Daltons.

In another preferred embodiment, the biobeneficial material can be a polyether such as poly(ethylene glycol) (PEG) or polyalkylene oxide.

Biocompatible Polymer

The biocompatible polymer useful in the coatings described herein can be any biocompatible polymer known in the art, which can be biodegradable or nondegradable. In some embodiments, the biocompatible polymer should have a $T_g$ above body temperature. Representative examples of polymers that can be used to coat an implantable device in accordance with the present invention include, but are not limited to, poly(ester amide), ethylene vinyl alcohol copolymer (commonly known by the generic name EVOH or by the trade name EVAL), poly(D,L-lactic acid), poly(L-lactic acid), poly(D-lactic acid), polycaprolactone, poly(hydroxyvalerate), poly(hydroxybutyrate), poly(hydroxybutyrate-co-valerate), polydioxanone, polyorthoester, polyanhydride, poly(glycolic acid), poly(D,L-lactic acid-co-glycolic acid) (PDLLAGA), poly(L-lactic acid-co-glycolic acid) (PLLAGA), poly(D-lactic acid-co-glycolic acid) (PDLAGA), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether; polyvinylidene halides, such as vinylidene fluoride based homo or copolymer under the trade name Solef™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

The biocompatible polymer can provide a controlled release of a bioactive agent, if included in the coating and/or if binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,581,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. One of ordinary skill in the art can readily select a carrier system using a biocompatible polymer to provide a controlled release of the bioactive agent.

A preferred biocompatible polymer is a polyester, such as one of poly(D,L-lactic acid) (PDLLA), poly(D-lactic acid) (PDLA), poly(L-lactic acid) (PLLA), poly(D,L-lactic acid-co-glycolic acid) (PDLLGA), poly(L-lactic acid-co-glycolic acid) (PLLGA), poly(D-lactic acid-co-glycolic acid) (PDLGA)—all of which are herein referred to as poly(lactic acid), poly(glycolic acid) (PGA), polyhydroxyalkanoate (PHA), poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), polycaprolactone (PCL), and a combination thereof.

Bioactive Agents

The polymeric coatings or the polymeric substrate described herein may optionally include one or more bioactive agents. These bioactive agents can be any agent which is a therapeutic, prophylactic, or diagnostic agent. These agents can have anti-proliferative or anti-inflammatory properties or can have other properties such as anti neoplastic, anti platelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following examples. All parameters and data are not to be construed to limit the scope of the embodiments of the invention.

Example 1

Effect of a PolyActive™ Top Coat on Coatings Formed of poly(D,L-lactic acid)

A. PENTA 13 mm stents (available from Guidant Corp.) were coated as follows:

A composition containing 300 µg poly(D,L-lactic acid) (PDLLA), 2% (w/w) in 1,1,2-trichloroethane (TCE)/chloroform (80/20) (1:1) was sprayed onto one stent. The coated stent was baked for about 60 minutes in an oven at a temperature of about 120° C.

B. PENTA 13 mm stents were coated as follows:

A composition containing 300 µg poly(D,L-lactic acid) (PDLLA), 2% (w/w) in 1,1,2-trichloroethan(TCE)/chloroform (80/20) (1:1) was sprayed onto one stent. The coated stent was baked for about 60 minutes in an oven at a temperature of about 120° C. The stents were then coated with a composition containing 150 µg PolyActive™ (300PEGT55PBT45) that contains 55% by weight PEGT segments and 45% by weight PBT segments in a concentration of 2% (w/w) in TCE/chloroform (80/20), and baked at 50° C. for 1 hour to allow the formation of a top layer of PolyActive™.

Figure 2A:
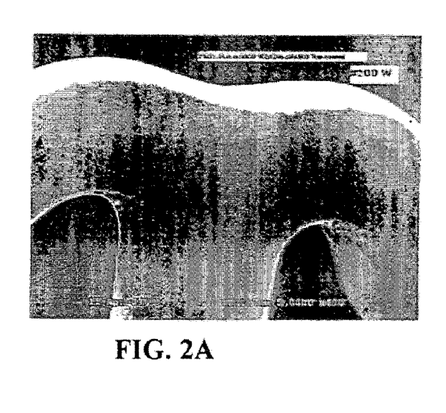
FIGS. 2A and 2B illustrate a stent coated with PDLLA and top-coated with PolyActive™ having a smooth surface after wet expansion.
Figure 2B:
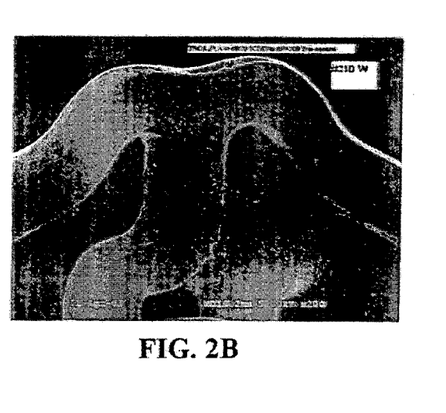

FIGS. 1A and 1B are SEM pictures of these stents coated with PDLLA only after crimping and wet expansion. The SEM pictures show some damages on the PLA coating. FIGS. 2A and 2B are pictures of the stents coated with a layer of PDLLA and a top coat of PolyActive™ after crimping and wet expansion. In contrast to the stents coated with PDLLA only, there is no sign of damage or peeling off of the coating at the surface on the stent top coated by PolyActive™.

Example 2

Effect of PolyActive™ on Coatings Formed of a Mixture of PDLLA and Polycaprolactone (PCL)

A. PENTA 13 mm stents were coated with PDLLA/PCL as follows:

The stents were primed with a composition containing 100 µg PCL (polycaprolactone) in a concentration of 2% (w/w) in TCE/xylene 70/30, baked at 50° C. for 1 hour to allow the formation of a primer layer of PCL. The stents were then coated with a composition containing 300 µg PDLLA-PCL (25/75) in a concentration of 2% (w/w) in TCE/chloroform (80/20), and baked at 50° C. for 1 hour to allow the formation of a layer of coating of PDLLA/PCL.

B. PENTA 13 mm stents were coated with PDLLA/PCL and a PolyActive™ topcoat as follows:

The stents were primed with a composition containing 100 µg PCL in a concentration of 2% (w/w) in tetrahydrofuran (THF)/xylene 70/30, baked at 50° C. for 1 hour to allow the formation of a layer comprising PCL. The stents were then coated with a composition containing 300 µg PDLLA-PCL (25/75) in a concentration of 2% (w/w) in TCE/chloroform (80/20), and baked at 50° C. for 1 hour to allow the formation of a layer of coating of PDLLA/PCL. The stents were top-coated with a composition containing 150 µg PolyActive™ (300PEGT55PBT45) (55% PEG and 45% PB) in a concentration of 2% (w/w) in TCE/chloroform (80/20), and baked at 50° C. for 1 hour to allow the formation of a layer of PolyActive™.

Figure 3A:
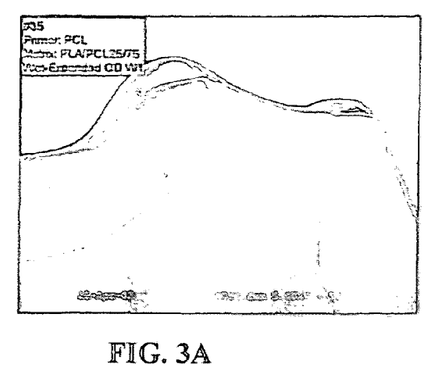
FIGS. 3A and 3B illustrate stents coated with polycaprolactone (PCL) primer and mixture of PDLLA and PCL after wet expansion, the surface being damaged at high strain regions.
Figure 3B:
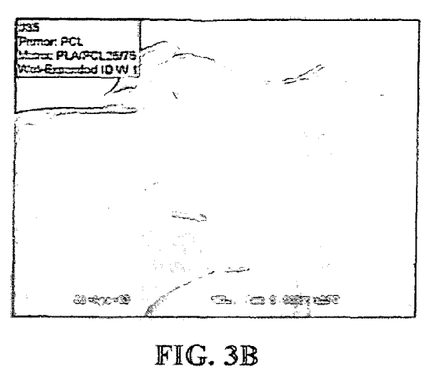
Figure 4A:
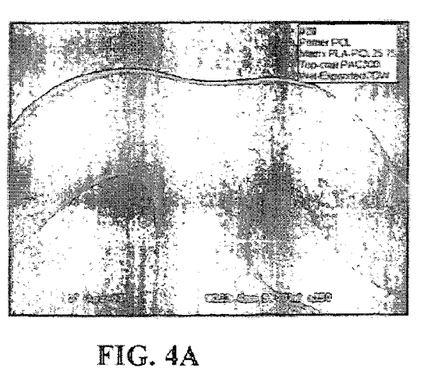
FIGS. 4A and 4B illustrate stents coated with PCL primer, PDLLA and PCL matrix and top coated with PolyActive™ after wet expansion, the surface being smooth with no sign of damage.
Figure 4B:
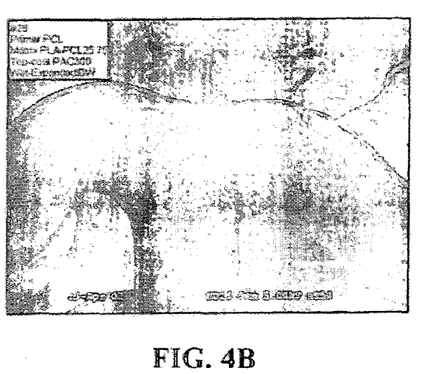

FIGS. 3A and 3B are pictures of stents coated with PDLLA/PCL after crimping and wet expansion, showing damages on the PDLLA/PCL coating. FIGS. 4A and 4B are pictures of the stents coated with PDLLA/PCL and a PolyActive™ topcoat, after crimping and wet expansion. In contrast to the stents shown in FIGS. 3A and 3B, there is no sign of damage or peeling off of the coating at the surface on the stent top coated by PolyActive™.

Example 3

Drug Delivery Stents Containing PolyActive™

VISION 12 mm small stents (available from Guidant Corp.) were coated with a process of the following steps: (1) priming with PolyActive™, (2) coating with everolimus, (3) coating with PLA, and (4) top-coating with PolyActive™. Each of the steps is described as follows.

Primer: the stents were primed with a composition containing 100 µg PolyActive™ (300PEGT55PBT45) (55% PEG and 45% PB) in a concentration of 2% (w/w) in TCE/chloroform 80/20, baked at 50° C. for 1 hour to form a PolyActive™ priming layer.

Drug matrix: The primed stents were coated with a composition containing 120 µg everolimus in a concentration of 2% (w/w) in acetone/xylene (60/40), and baked at 50° C. for 1 hour to allow the formation of a layer of drug coating.

PLA layer: The stents coated with everolimus were coated with a composition containing 75 µg PLA in a concentration of 2% by weight dissolved in a solvent mixture of TCE/chloroform (80/20), and baked at 50° C. for 1 hour to allow the formation of a layer of PLA.

PolyActive™ topcoat: The stents were top-coated with a composition containing 300 µg PolyActive™ (300PEGT55PBT45) (55% PEG and 45% PB) in a concentration of 2% (w/w) in TCE/chloroform (80/20), and baked at 50° C. for 2 hour to allow the formation of a layer of PolyActive™.

Figure 5A:
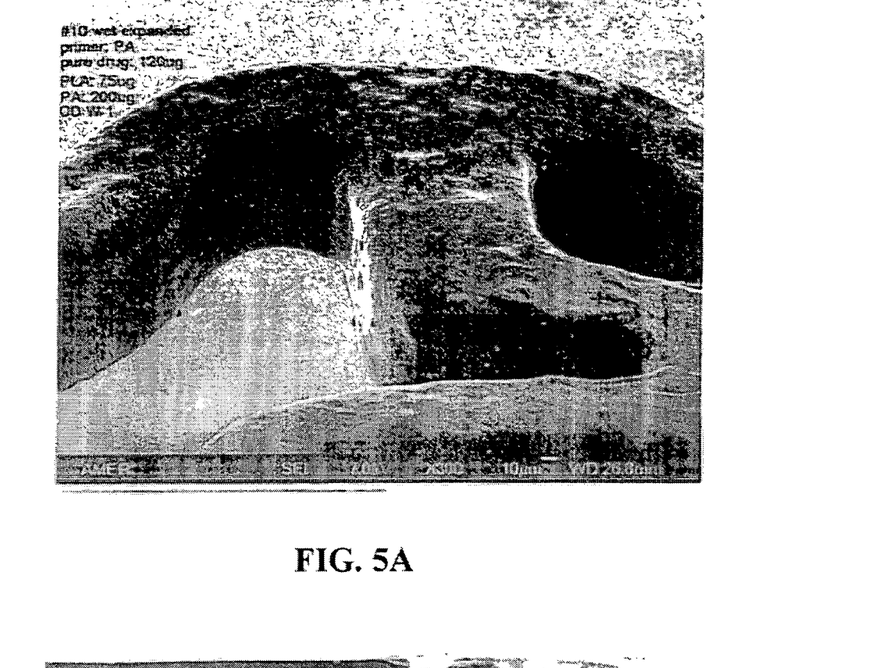
FIGS. 5A and 5B are scanning electronic micrograph (SEM) images for OD surface (FIG. 5A) and ID surface (FIG. 5B) of coating first with PolyActive™ as primer, second with everolimus, third with PLA, and finally again with PolyActive™.
Figure 5B:
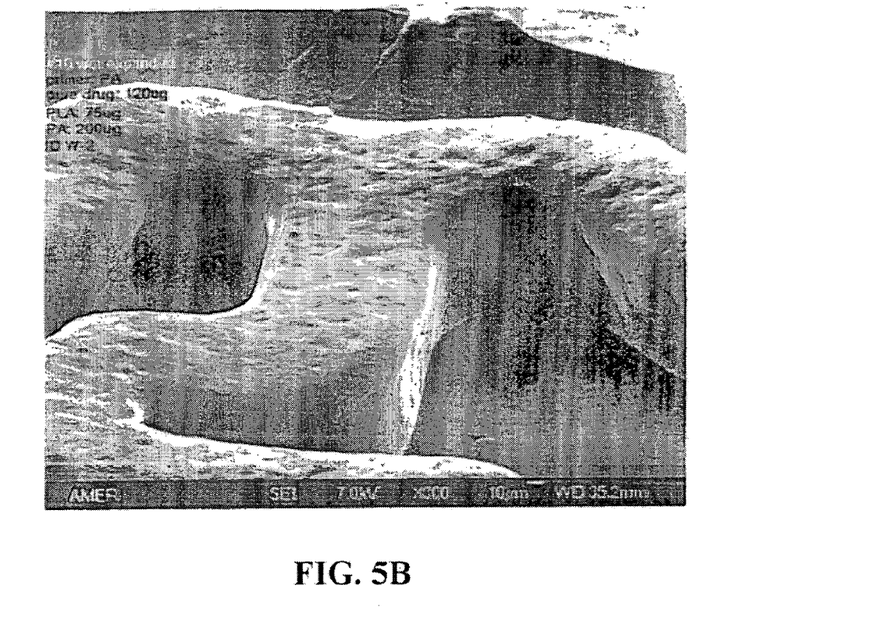

FIGS. 5A and 5B are SEM images of the stents after wet expansion. The images show good surface properties of the stents. The stents were tested for drug release in vitro, which showed a release of 30% of drug load at 24 hour, using porcine serum as the release media.

Example 4

Drug-Delivery Coatings Including a PolyActive™ Topcoat

A. VISION 12 mm small stents can be coated with a process of the following steps: (1) priming with PolyActive™, (2) coating with everolimus and PLA, and (3) top-coating with PolyActive™ Each of the steps is described as follows.

Primer: The stents can be primed with a composition containing 100 µg PolyActive™ (300PEGT55PBT45) (55% PEG and 45% PB) in a concentration of 2% (w/w) in TCE/chloroform 80/20, baked at 50° C. for 1 hour to allow the formation of a primer layer of PolyActive™.

Drug matrix: The primed stents can be coated with a composition containing a 240 µg mixture of everolimus (120 µg) and PLA (120 µg) (everolimus/PLA=1:1) in acetone/cyclohexane (70/30), and baked at 50° C. for 2 hour to allow the formation of a layer of coating of everolimus and PLA.

PolyActive™ topcoat: The stents can be top-coated with a composition containing 300 µg PolyActive™ (300PEGT55PBT45) (55% PEG and 45% PB) in a concentration of 2% (w/w) in TCE/chloroform (80/20), and baked at 50° C. for 2 hour to allow the formation of a layer of PolyActive™.

B. Alternatively, VISION 12 mm small stents can be coated without a layer of PolyActive™ primer: (1) coating with everolimus and PLA, and (2) top-coating with PolyActive™. Each of the steps is described as follows.

Drug matrix: The stents can be coated with a composition containing a 200 µg mixture of everolimus and PLA (everolimus/PLA=2:1) in acetone/cyclohexane (70/30), and baked at 50° C. for 2 hour to allow the formation of a layer of coating of everolimus and PLA.

PolyActive™ topcoat: The stents can be top-coated with a composition containing 300 µg PolyActive™ (300PEGT55PBT45) (55% PEG and 45% PB) in a concentration of 2% (w/w) in TCE/chloroform (80/20), and baked at 50° C. for 2 hour to allow the formation of a layer of PolyActive™.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device comprising:
   a first component including a block copolymer including blocks of poly(ethylene glycol) and poly(butylene terephthalate);
   a second component including polylactic acid; and
   a third component including a bioactive agent, wherein the first component is coating regions beneath and above the second component.

2. A coating for an implantable medical device comprising:
   a first component including a block copolymer including blocks of poly(ethylene glycol) and poly(butylene terephthalate);
   a second component including polylactic acid; and
   a third component including a bioactive agent,
   wherein the medical device comprises a body structure aside from the coating.

3. The coating of claim 2, wherein the polylactic acid is poly(L-lactic acid), poly(D,L-lactic acid) or poly(D-lactic acid).

4. The coating of claim 2, wherein the second and third components are blended and the first component is a coating region over the second and third components.

5. The coating of claim 2, wherein the device is a stent.

6. The coating of claim 2, wherein the first component is an AB, ABA or a BAB block copolymer.

7. A coating for an implantable medical device comprising:
- a first component including a block copolymer including blocks of poly(ethylene glycol) and poly(butylene terephthalate);
- a second component including polylactic acid; and
- a third component including a bioactive agent, wherein the second and third components are blended and the first component is coating regions beneath and over the second and third components.

8. A coating for an implantable medical device comprising:
- a first layer including a polylactic acid; and
- a second layer of a block copolymer including blocks of poly(ethylene glycol) and poly(butylene terephthalate) supported by the first layer of polylactic acid,
- wherein the medical device comprises a body structure aside from the coating.

9. A coating for an implantable medical device comprising:
- a first layer including a polylactic acid;
- a second layer of a block copolymer including blocks of poly(ethylene glycol) and poly(butylene terephthalate) supported by the first layer of polylactic acid; and
- a third layer of a block copolymer including blocks of poly(ethylene glycol) and poly(butylene terephthalate) disposed beneath the first layer of polylactic acid.

10. The coating of claim 8, additionally comprising a drug.

11. The coating of claim 8, wherein the polylactic acid is poly(L-lactic acid), poly(D,L-lactic acid) or poly(D-lactic acid).

12. A coating for an implantable medical device comprising:
- a first component including blocks which include poly(ethylene glycol) and blocks which include terephthalate;
- a second component including polylactic acid; and
- a third component including a bioactive agents
- wherein the medical device comprises a body structure aside from the coating.

* * * * *